United States Patent [19]

Franz et al.

[11] Patent Number: 4,556,415

[45] Date of Patent: Dec. 3, 1985

[54] BIS-(ALKOXY)TETRATHIOTRICARBOXY-LATES AND USE AS HERBICIDES THEREOF

[75] Inventors: John E. Franz, Crestwood; Kurt E. Zwikelmaier, St. Louis, both of Mo.

[73] Assignee: Monsanto Company, St. Louis, Mo.

[21] Appl. No.: 723,237

[22] Filed: Apr. 15, 1985

[51] Int. Cl.[4] .................... C07C 154/02; A01N 37/00; A01N 37/12
[52] U.S. Cl. ................................. 71/100; 260/455 B; 71/101; 71/102
[58] Field of Search .............. 260/455 B; 71/100, 101, 71/102

[56] References Cited

PUBLICATIONS

Friederang, et al., Tetrahedron Letters, 55, pp. 5535–5536.
Dean, et al., Chemical Communications, (1969), pp. 728–729.
Dean, et al., J. Org. Chem., 36, pp. 1180–1183.

Primary Examiner—Henry R. Jiles
Assistant Examiner—Robert C. Whittenbaugh
Attorney, Agent, or Firm—Frank D. Shearin; Richard H. Shear; Arnold H. Cole

[57] ABSTRACT

Bis-(alkoxy)tetrathiotricarboxylates are disclosed as well as herbicidal compositions containing such compounds and the use of such compounds as post-emergence herbicides.

28 Claims, No Drawings

BIS-(ALKOXY)TETRATHIOTRICARBOXYLATES AND USE AS HERBICIDES THEREOF

BACKGROUND OF THE INVENTION

The present invention is directed to bis-(alkoxy)tetrathiotricarboxylates as well as herbicidal compositions containing these compounds and the use of these compounds as post-emergence herbicides.

It has been predicted that the reaction of potassium ethylxanthate and phosgene would produce bis(ethoxy)tetrathiotricarboxylate. It is reported in Willcox, (1906) *J. Amer. Chem. Soc.* 28:1031–1034, however, that the expected product was not obtained, the reaction being "complex" in nature. Zhuravlev and Galchenko, (1947) *Zhurnal Prikladnoi Khimii*, pp. 1038–1043 report that the reaction produces xanthogenic thioanhydride, potassium chloride, and carbonyl sulfide. There appears to be a suggestion in the paper that the tetrathiotricarboxylate is an unstable intermediate in the reaction. There is no evidence reported, however, indicating that the tetrathiotricarboxylate was formed.

The preparation of dialkyltricarbonates and corresponding dialkyl dithioltricarbonates is known in the art. For examples, Friederang and Tarbell, (1968) *Tetrahedron Letters* 55:5535–5536, discloses the synthesis of di-t-butyl dithioltricarbonate from the reaction of sodium t-butyl thiolcarbonate and phosgene. Dean and Tarbell, *Chemical Communications* 1969:728–729, discloses the preparation of di-t-butyl tricarbonate as well as di-isopropyl dithioltricarbonate and di-isopropyl tricarbonate. The isopropyl compounds, however, could not be obtained in pure form because they decomposed to their corresponding dicarbonates.

The reaction products of dialkyl tricarbonates and dialkyl dithiotricarbonates with alcohols, mercaptans, primary amines and secondary amines have also been reported. The reaction of the di-ty-butyl compounds with alcohols and mercaptans yields mixed dicarbonates, reaction with primary amines yields isocyanates via a carbonic carbamic anhydride intermediate, and reaction with secondary amines yields carbamic anhydrides. See Dean and Tarbell, (1971) *J. Org. Chem.* 36:1180–1183.

DETAILED DESCRIPTION OF THE INVENTION

Applicants' invention relates to post-emergence herbicides of the class of compounds bis-(alkoxy)tetrathiotricarboxylates represented by the structure

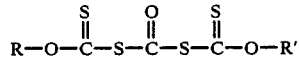

wherein R and R', which can be the same or different, are selected from alkyl groups having from 1 to 8 carbon atoms, and alkenyl groups having from 2 to 8 carbon atoms, and cycloalkyl groups having 3 to 8 carbon atoms. Other embodiments of the present invention include herbicidal compositions comprising the above bis-(alkoxy)tetrathiotricarboxylates, and methods of controlling plants which comprises contacting plants with the above bix-(alkoxy)tetrathiotricarboxylates.

Preferably, R and R' are selected from alkyl groups, having 1 to 6 carbon atoms, alkenyl groups and alkoxyalkyl groups having 2 to 6 carbon atoms, and cycloalkyl groups having 3 to 6 carbon atoms. Most preferably, R and R' are selected from alkyl groups, having 1 to 4 carbon atoms, alkenyl groups and alkoxyalkyl groups with 2 to 4 carbon atoms, and cycloalkyl groups with 3 to 4 carbon atoms.

Where R and R' are selected from alkyl groups, these groups can include, but are not limited to, branched and straight chained alkyl radicals, such as methyl, ethyl, n-propyl, isopropyl, n-butyl, isobutyl, tert-butyl, amyl, isoamyl, 2-methylbutyl, 1,1-dimethylpropyl, 2,2-dimethylpropyl, n-hexyl, isohexyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 2,3-dimethylbutyl, heptyl, 1-methylhexyl, 2-methylhexyl, 3-methylhexyl, 4-methylhexyl, 5-methylhexyl, 1,1-dimethylpentyl, 2,2-dimethylpentyl, 3,3-dimethylpentyl, 4,4-dimethylpentyl, 1,3-dimethylpentyl, 1,4-dimethylpentyl, 2,3-dimethylpentyl, 2,4-dimethylpentyl, 3,4-dimethylpentyl, 1,2,3,-trimethylbutyl, 1,2,2-trimethylbutyl, 1,3,3-trimethylbutyl, 2,3,3-trimethylbutyl, 2,2,3-trimethylbutyl, octyl, 1-methylheptyl, 2-methylheptyl, 3-methylheptyl, 4-methylheptyl, 5-methylheptyl, 6-methylheptyl, 1,1-dimethylhexyl, 2,2-dimethylhexyl, 3,3-dimethylhexyl, 4,4-dimethylhexyl, 1,2-dimethylhexyl, 1,3-dimethylhexyl, 1,4-dimethylhexyl, 1,5-dimethylhexyl, 2,3-dimethylhexyl, 2,4-dimethylhexyl, 2,5-dimethylhexyl, 3,4-dimethylhexyl, 3,5-dimethylhexyl, 4,5-dimethylhexyl, 1-ethylhexyl, 2-ethylhexyl, 3-ethylhexyl, 4-ethylhexyl, trimethylamyls, methylethylamyls, propylamyls, tetramethylbutyls, diethylbutyls, and methylpropylbutyls.

Where R and R' are selected from alkenyl groups, these groups can include, but are not limited to, vinyl, 1-propenyl, allyl, isopropenyl, 1-butenyl, 2-butenyl, 3-butenyl, 1-methyl-1-propenyl, 1,3-butadienyl, 1-pentenyl, 2-pentenyl, 3-pentenyl, 4-pentenyl, 1-methyl-1-butenyl, 3-methyl-1-butenyl, 1,4-pentadienyl, 2,3-pentadienyl, 2,4-pentadienyl, 1-hexenyl, 2-hexenyl, 3-hexenyl, 4-hexenyl, 5-hexenyl, 1-methyl-1-pentenyl, 1-ethyl-1-butenyl, 1-propyl-1-propenyl, 4-methyl-1-pentenyl, 1,3-hexadienyl, 1,4-hexadienyl, 1,5-hexadienyl, 2,3-hexadienyl, and 2,4-hexadienyl.

Wherein R and R' are selected from the group of cycloalkyls, these groups can include, but are not limited to, cyclopropyl, cyclobutyl, cyclopentyl, cyclohexyl, 2-methyl-cyclohexyl, 2,6-dimethyl cyclohexyl, 3,4-dimethyl cyclohexyl, cycloheptyl, and cyclooctyl.

The compounds of the present invention can be synthesized by reacting a substituted xanthate suspended in dry ether with phosgene at ambient temperature. The phosgene may be bubbled into the salt suspension or fed dropwise in solution with toluene. Generally, the xanthate is the sodium, lithium, or potassium salt of the corresponding xanthic acid.

Furthermore, it has been found that compounds of the present invention can be used as post-emergence herbicides on weed species, such as cocklebur, valvetleaf, common lambsquarters, barnyardgrass, hemp sesbania, and large crabgrass in crops, such as wheat, rice, and grain sorghum, as shown in the data below. Of course, the weed/crop combination(s) for which a particular tetrathiotricarboxylate is suited will vary and should be determined on an individual basis for each compound.

The following examples illustrate the preparation of compounds within the scope of the present invention and their activity as post-emergence herbicides. The examples are included for illustrative purposes only and are not intended to limit the scope of the invention.

EXAMPLE 1

Preparation of Bis-(Ethoxy)Tetrathiotricarboxylate

Ten grams (0.0625 mole) of potassium ethylxanthate was suspended at ambient temperature in 100 ml of ether and stirred. Then a solution of phosgene (2.8 g, 0.028 mole) in 35 ml of toluene was added to the xanthate suspension dropwise over a 10 minute period. The suspension was stirred for an additional 45 minutes and then filtered to remove 6.2 g of precipitated potassium chloride. The filtrate was stripped of solvent to yield 6.7 g of yellow oil as a final product. The yellow oil was insoluble in water but soluble in chloroform. Elemental analysis indicated that the oil was the desired product having an analysis as follows:

Calc'd for $C_7H_{10}O_3S_4$: C, 31.09; H, 3.73. Found: C, 31.16; H, 3.82.

EXAMPLE 2

Preparation of Bis-(n-Propoxy)Tetrathiotricarboxylate

To 30 g (0.17 mole) of potassium n-propyl xanthate suspended in 250 ml of ether there was added dropwise 7.8 g of phosgene in 109 ml of toluene dropwise over a period of about 30 minutes. The reaction mixture, after the addition of phosgene was stirred 20 minutes and filtered to remove potassium chloride. The filtrate was stripped of solvent to yield 19.12 g of a yellow oil. The yellow oil was insoluble in water but soluble in chloroform. Elemental analysis indicated that the oil was the desired product having an analysis as follows:

Calc'd for $C_9H_{14}O_3S_4$: C, 36.22; H, 4.73. Found: C, 36.34; H, 4.78.

EXAMPLE 4

Preparation of Bis-(n-Butoxy)Tetrathiotricarboxylate

Potassium butylxanthate (30 g) was suspended in ether and phosgene gas bubbled through the suspension for 1 hour while being cooled in a water bath. After the addition of the gas, the suspension was purged with nitrogen gas for 10 minutes and then filtered to remove the precipitated potassium chloride (12 g). The filtrate was then stripped of solvent to yield a yellow liquid.

Mass spectral analysis showed the oil to have a molecular ion peak at m/e 212 which corresponds to the structure n-BuOC(S)SC(O)Cl. Infrared spectroscopy showed 2 carbonyl bands, one at 5.58 and the other at 5.73. The peak at 5.58 corresponds to the structure above. The peak at 5.73 corresponds to the structure [n-BuOC(S)S]$_2$CO; i.e., bis-(n-butoxy)tetrathiotricarboxylate. The oil was then taken up in ether and an additional 10 g of potassium butylxanthate added. After 20 minutes, the IR band at 5.58 had disappeared and the one at 5.73 was intensified. The suspension was filtered to remove 5.85 g of solid and the filtrate stripped of solvent to yield 29.05 g of the yellow oil. The yellow oil was insoluble in water but soluble in acetone and chloroform. Elemental analysis showed the oil to be in the desired product having an analysis as follows:

Calc'd for $C_{11}H_{18}O_3S_4$: C, 40.46; H, 5.56. Found: C, 40.72; H, 5.61.

The compounds prepared in the above example are summarized in Table I.

TABLE I

| RUN No. | Compound | Structure |
|---|---|---|
| A | bis-(ethoxy)tetrathiotricarboxylate | $C_2H_5-\overset{\overset{S}{\|\|}}{O}C\overset{\overset{O}{\|\|}}{S}C\overset{\overset{S}{\|\|}}{S}CO-C_2H_5$ |
| B | bis-(n-propoxy)tetrathiotricarboxylate | $CH_3(CH_2)_2-\overset{\overset{S}{\|\|}}{O}C\overset{\overset{O}{\|\|}}{S}C\overset{\overset{S}{\|\|}}{S}CO-(CH_2)_2CH_3$ |
| C | bis-(isopropoxy)tetrathiotricarboxylate | $(CH_3)_2CH-\overset{\overset{S}{\|\|}}{O}C\overset{\overset{O}{\|\|}}{S}C\overset{\overset{S}{\|\|}}{S}CO-CH(CH_3)_2$ |
| D | bis-(n-butoxy)tetrathiotricarboxylate | $CH_3(CH_2)_3-\overset{\overset{S}{\|\|}}{O}C\overset{\overset{O}{\|\|}}{S}C\overset{\overset{S}{\|\|}}{S}CO-(CH_2)_3CH_3$ |

Calc'd for $C_9H_{14}O_3S_4$: C, 36.22; H, 4.73. Found: C, 36.39; H, 4.80.

EXAMPLE 3

Preparation of Bis-(Isopropoxy)Tetrathiotricarboxylate

To 15 g (0.56 mole) of potassium isopropylxanthate suspended in 100 ml of ether with stirring was added dropwise a solution of 3.9 g (0.039 mole) of phosgene in 57 ml of toluene over a period of 15 minutes. Stirring was continued for 20 minutes after the addition was completed. The suspension was then filtered to remove the potassium chloride (8.0 g). Then the filtrate was stripped of solvent to yield a yellow oil. The yellow oil was insoluble in water but soluble in acetone and chloroform. Elemental analysis demonstrated the compound was bis-(isopropoxy)tetrathiotricarboxylate having an analysis as follows:

EXAMPLE 5

Post-Emergence Herbicidal Activity

The post-emergence herbicidal activity of compounds in Table I was demonstrated by greenhouse testing in the following manner. A good grade of top soil is placed in aluminum pans having holes in the bottom and compacted to the depth of 0.95 to 1.27 cm from the top of the pan. A predetermined number of seeds of each of several dicotyledonous and monocotyledonous annual plant species and/or vegetative propagules for the perennial plant species were placed on the soil and pressed into the soil surface. The seeds and/or vegetative propagules are covered with soil and leveled. The pans are then placed on the sand bench in the greenhouse and watered from below as needed. After the plants reach the desired age (two to three weeks) each pan, except for the control pans, is removed individually to a spraying chamber and sprayed by means of an atomizer at the rates noted. In the spray solution is an amount of an emulsifying agent mixture to give a spray solution or suspension which contains about 0.4% by weight of the emulsifier. The spray solution or suspension contains a sufficient amount of the candidate chemical in order to give application rates corresponding to those set forth in the tables. The pans were returned to the greenhouse and watered as before and the injury to the plants as compared to the control is observed at approximately two weeks and the results recorded.

The post-emergence herbicidal activity index used in Tables II and III is as follows:

| Plant Response | Index |
| --- | --- |
| 0–24% Inhibition | 0 |
| 25–49% Inhibition | 1 |
| 50–74% Inhibition | 2 |
| 75–99% Inhibition | 3 |
| 100% Inhibition | 4 |
| No Data | N |

The plant species utilized in these tests are identified by letter in accordance with the following legend:

A — Canada Thistle*  K — Barnyardgrass
B — Cocklebur  L — Soybean
C — Velvetleaf  M — Sugar Beet
D — Morningglory  N — Wheat
E — Common Lambsquarter  O — Rice
F — Pennsylvania Smartweed  P — Grain Sorghum
G — Yellow Nutsedge*  Q — Wild Buckwheat
H — Quackgrass*  R — Hemp Sesbania
I — Johnsongrass*  S — Proso Millet
J — Downy Brome  T — Large Crabgrass

*Established from vegetative propagules

TABLE II

| Post-Emergence Activity at 11.2 kg/h | | | | | | | | | | |
| --- | --- | --- | --- | --- | --- | --- | --- | --- | --- | --- |
| Plant | | | | | | | | | | |
| Compound | A | B | C | D | E | F | G | H | I | J | K |
| Ex. 1 | 0 | 2 | 2 | 1 | 4 | N | 0 | 0 | 0 | 0 | 1 |
| Ex. 2 | 1 | 2 | 2 | 1 | 3 | 4 | 0 | 1 | 1 | 0 | 1 |
| Ex. 3 | 2 | 3 | 3 | 1 | 4 | N | 0 | 0 | 0 | 1 | 3 |
| Ex. 4 | 2 | 2 | 2 | 2 | 4 | 0 | 0 | 1 | 0 | 1 | 1 |

TABLE III

| Post-Emergence Activity at 5.6 kg/h | | | | | | | | | | | | | |
| --- | --- | --- | --- | --- | --- | --- | --- | --- | --- | --- | --- | --- | --- |
| Plant | | | | | | | | | | | | | |
| Compound | B | C | D | E | J | K | L | M | N | O | P | Q | R | S | T |
| Ex. 2 | 2 | 2 | 1 | 4 | 0 | 1 | 2 | 1 | 0 | 0 | 0 | 2 | 2 | 1 | 1 |
| Ex. 3 | 2 | 4 | 2 | 4 | 2 | 2 | 2 | 3 | 1 | 0 | 0 | 2 | 4 | 2 | 4 |

EXAMPLE 6

Preparation of Bis-(Methoxy)Tetrathiotricarboxylate

In a 250 ml round bottomed flask was placed a solution of 2.25 g (0.0227 mole) of phosgene in 60 g diethyl ether and 50 g toluene. The solution in the flask was cooled to 0° C. in an ice bath, and 6.3 (0.0432 mole) of potassium methylxanthate was added to the solution dropwise over a five-minute period with stirring. The solution was stirred for an additional 25 minutes and then filtered to remove potassium chloride. The solvent was evaporated to yield a crude solid. The solid was dissolved in ethyl acetate and precipitated with benzene. The purified solid had a melting point of 62.5°–65.0° C. Infrared spectroscopy confirmed the structure of the desired compound.

The post-emergence herbicidal activity of bis-(methoxy)tetrathiotricarboxylate was demonstrated at two different rates using the procedure of Example 5, except that the compound was formulated immediately prior to spraying. The results are shown in TABLE IV.

TABLE IV

| Post-Emergent Activity of Bis-(methoxy)-tetrathiotricarboxylate | | | | | | | | | | | |
| --- | --- | --- | --- | --- | --- | --- | --- | --- | --- | --- | --- |
| Plants | | | | | | | | | | | |
| Rate (kg/h) | A | B | C | D | E | F | G | H | I | J | K |
| 56.1 | 4 | 3 | 3 | 3 | 4 | 3 | 1 | 1 | 0 | 2 | 3 |
| 22.4 | 0 | 3 | 0 | 0 | 4 | 2 | 0 | 0 | 0 | 1 | 1 |

From the test results presented in the tables, it can be seen that the compounds of the present invention have post-emergence herbicidal activity.

Typically, herbicidal compounds of this invention are provided in the form of concentrates which require dilution prior to application to plants. The usual means for diluting the herbicide is the preparation of herbicidal compositions wherein the compound possessing herbicidal activity is mixed with other materials. Such other materials may be in either liquid or solid form and comprise adjuvants, inert materials, etc.

The herbicidal composition containing herbicidal compounds of this invention are prepared in the usual manner by combining them with other materials which are well known in the herbicide art. The following is a description of herbicidal compositions employing the herbicidal compounds of this invention together with known materials and formulations typically utilized in the herbicide art.

The herbicidal compositions, including concentrates which require dilution prior to application to the plants, of this invention contain from 5 to 95 parts by weight of at least one compound of this invention and from 5 to 95 parts by weight of an adjuvant in liquid or solid form, for example, from about 0.25 to 25 parts by weight of wetting agent, from about 0.25 to 25 parts by weight of a dispersant, and from 4.5 to about 94.5 parts by weight of an inert liquid extender (e.g., water, acetone, tetrahydrofuran), all parts being by weight of the total composition. Preferably, the compositions of this invention contain from 5 to 75 parts by weight of at least one compound of this invention, together with the adjuvants. Where required, from about 0.1 to 2.0 parts by weight of the inert liquid extender can be replaced by a corrosion inhibitor, such as ethanol mercaptan, sodium thiosulfate, or an anti-foaming agent such as a dimethylpolysiloxane or both. The compositions are prepared by admixing the active ingredient with an adjuvant including diluents, extenders, carriers, and conditioning agents to provide a composition in the form of finely-divided solid, a liquid of organic origin, water, a wetting agent, a dispersing agent, an emulsifying agent, or any suitable combination of these.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhance their efficacy. By the term "surface-active agent" it is understood that wetting agents, dispersing agents, suspending agents, and emulsifying agents are included therein. Anionic, cationic, and nonionic agents can all be used.

Preferred wetting agents are alkyl benzene and alkyl naphthalene sulfonates, sulfated fatty alcohols, amines or acid amides, long-chain acid esters of sodium isothionate, esters of sodium sulfosuccinate, sulfated or sulfonated fatty acid esters, petroleum sulfonates, sulfonated vegetable oils, polyoxyethylene derivatives of phenols and alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, sodium lignosulfonates, polymeric alkyl naphthalene sulfonates, sodium naphthalene sulfonate, polymethylene bisnaphthalenesulfonate and sodium N-methyl-N-(long chain acid)laurates.

The application of an effective amount of the compounds or compositions of this invention to the plant is essential and critical for the practice of the present invention. The exact amount of active ingredient to be employed is dependent upon the response desired in the plant as well as such other factors as the plant species and stage of development thereof, and the amount of rainfall as well as the specific bis-(alkoxy)tetrathiotricarboxylate employed. In foliar treatment for the control of vegetative growth, the active ingredients are applied in amounts from about 0.112 to about 56.0 or more kilograms per hectare. An effective amount for phytotoxic or herbicidal control is that amount necessary for overall or selective control, i.e., a phytotoxic or herbicidal amount. One skilled in the art can readily determine from the teachings of this specification, including examples, the appropriate application rate.

Although this invention has been described with respect to specific illustrative embodiments, the details thereof are not to be construed as limitations, for it will be apparent that various equivalents, changes, and modifications may be resorted to without departing from the spirit and scope thereof, and it is understood that such equivalent embodiments are intended to be included herein.

We claim:

1. A compound represented by the structure

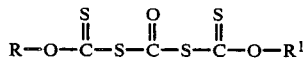

wherein R and R' are independently selected from alkyl groups having 1 to 8 carbon atoms and alkenyl groups having 2 to 8 carbon atoms and cycloalkyl groups having 3 to 8 carbon atoms.

2. A compound of claim 1 wherein R and $R^1$ are independently selected from alkyl groups having 1 to 6 carbon atoms, and alkenyl groups having 2 to 6 carbon atoms and cycloalkyl groups having 3 to 6 carbon atoms.

3. A compound of claim 1 wherein R and $R^1$ are independently selected from alkyl groups having 1 to 8 carbon atoms.

4. A compound of claim 1 wherein R and $R^1$ are independently selected from alkyl groups having 1 to 6 carbon atoms.

5. A compound of claim 1 wherein R and $R^1$ are independently selected from alkyl groups having 1 to 4 carbon atoms.

6. A compound of claim 5 wherein R and $R^1$ are methyl.

7. A compound of claim 5 wherein R and R' are ethyl.

8. A compound of claim 5 wherein R and $R^1$ are n-propyl.

9. A compound of claim 5 wherein R and $R^1$ are isopropyl.

10. A compound of claim 5 wherein R and $R^1$ are n-butyl.

11. A herbicidal composition which comprises an inert adjuvant and a herbicidally effective amount of the compound of claim 1.

12. A herbicidal composition of claim 1 which comprises a herbicidally effective amount of the compound of claim 2.

13. A herbicidal composition of claim 1 which comprises a herbicidally effective amount of the compound of claim 3.

14. A herbicidal composition of claim 1 which comprises a herbicidally effective amount of the compound of claim 4.

15. A herbicidal composition of claim 1 which comprises a herbicidally effective amount of the compound of claim 5.

16. A herbicidal composition of claim 1 which comprises a herbicidally effective amount of the compound of claim 6.

17. A herbicidal composition of claim 1 which comprises a herbicidally effective amount of the compound of claim 7.

18. A herbicidal composition of claim 1 which comprises a herbicidally effective amount of the compound of claim 8.

19. A herbicidal composition of claim 1 which comprises a herbicidally effective amount of the compound of claim 9.

20. A method which comprises contacting weeds with a herbicidally effective amount of the compound of claim 1.

21. A method of claim 20 wherein weeds are contacted with a herbicidally effective amount of the compound of claim 2.

22. A method of claim 20 wherein weeds are contacted with a herbicidally effective amount of the compound of claim 3.

23. A method of claim 20 wherein weeds are contacted with a herbicidally effective amount of the compound of claim 4.

24. A method of claim 20 wherein weeds are contacted with a herbicidally effective amount of the compound of claim 5.

25. A method of claim 20 wherein weeds are contacted with a herbicidally effective amount of the compound of claim 6.

26. A method of claim 20 wherein weeds are contacted with a herbicidally effective amount of the compound of claim 7.

27. A method of claim 20 wherein weeds are contacted with a herbicidally effective amount of the compound of claim 8.

28. A method of claim 20 wherein weeds are contacted with a herbicidally effective amount of the compound of claim 9.

* * * * *